(12) United States Patent
Heslet et al.

(10) Patent No.: US 7,807,639 B2
(45) Date of Patent: Oct. 5, 2010

(54) METHODS FOR PREVENTING AND TREATING LOCAL TRACHEAL, BRONCHIAL OR ALVEOLAR BLEEDING OR HEMOPTYSIS

(75) Inventors: Lars Heslet, Gentofte (DK); Lars Otto Uttenthal, Salamanca (ES)

(73) Assignee: Pharmaorigin ASP, Gentofte (DK)

( * ) Notice: Subject to any disclaimer, the term of this patent is extended or adjusted under 35 U.S.C. 154(b) by 0 days.

(21) Appl. No.: 11/442,474

(22) Filed: May 26, 2006

(65) Prior Publication Data

US 2007/0060517 A1     Mar. 15, 2007

Related U.S. Application Data

(63) Continuation-in-part of application No. PCT/DK2005/000576, filed on Sep. 9, 2005.

(60) Provisional application No. 60/693,969, filed on Jun. 24, 2005, provisional application No. 60/622,977, filed on Oct. 28, 2004, provisional application No. 60/608,759, filed on Sep. 10, 2004.

(51) Int. Cl.
   *A61K 38/36* (2006.01)
(52) U.S. Cl. .............................. 514/12; 514/2; 530/384; 424/9.1
(58) Field of Classification Search .................. 514/12, 514/2; 530/384; 424/9.1
See application file for complete search history.

(56) References Cited

U.S. PATENT DOCUMENTS

| | | | |
|---|---|---|---|
| 3,920,845 A | 11/1975 | Smith et al. | 424/331 |
| 5,096,916 A | 3/1992 | Skupin | 514/401 |
| 5,427,797 A | 6/1995 | Frostell et al. | 424/434 |
| 5,690,910 A | 11/1997 | Ahmed et al. | 424/45 |
| 5,980,865 A | 11/1999 | Ahmed | 424/45 |
| 6,193,957 B1 | 2/2001 | Ahmed | 424/45 |
| 6,497,877 B1 | 12/2002 | Stringer et al. | 424/94.64 |
| 2003/0054018 A1 | 3/2003 | Hedner | |
| 2003/0195141 A1 | 10/2003 | Mathison | 514/2 |
| 2004/0265238 A1 | 12/2004 | Chaudry | 424/45 |
| 2005/0008580 A1 | 1/2005 | Gong et al. | 424/46 |
| 2005/0059590 A1* | 3/2005 | Pan et al. | 514/12 |

OTHER PUBLICATIONS de Gracia et al. Use of endoscopic fibrinogen-thrombin in the treatment of severe hemoptysis. (Apr. 2003) vol. 97: 790-795.* de Gracia et al., "The use of fibrinogen-thrombin via endoscope in the treatment of massive hemoptysis", Arch Bronconeumol. 1995 31(5):27-232 (Abstract only).

de Gracia et al., "Use of endoscopic fibrinogen-thrombin in the treatment of severe hemoptysis", Respir Med. 2003 97(7):790-795 (Abstract only).

Henke et al., "Successful Treatment of Diffuse Alveolar Hemorrhage with Activated Factor VII", Annals of Internal Medicine 2004 140(6):493-494.

Hosoda et al., "A frequent fiber-scopic bronchial lavage for the case of bilateral sever pulmonary contusion with flail chest", Kyobu Geka. 2001 54(4):352-354 (Abstract only).

Pastores et al., "Diffuse Alveolar Hemorrhage After Allogeneic Hematopoietic Stem-Cell Transplantation", Chest 2003 124:2400-2403.

Saito et al., "Pulmonary pseudallescheriasis in a patient with diabetes mellitus and alcoholic liver cirrhosis", Nihon Kokyuki Gakkai Zasshi 1998 36(5):498-502 (Abstract only).

Betensley et al., "Factor VIIa for Alveolar Hemorrhage in Microscopic Polyangitis", American Journal of Respiratory and Critical Care Medicine 2002 166:1291-129.

Dvilansky et al., "Factor XIII Assay by an Isotope Method—I. Factor XIII (Transamidase) in Plasma, Serum, Leucocytes, Erythrocytes and Platelets and Evaluation of Screening Tests of Clot Solubility", British Journal of Haematology 1970 18:399-410.

Ghorashian et al., "Off-license" use of recombinant activated factor VII, Blood Reviews 2004 18:245-259.

Tsukamoto et al., "Treatment of Hemoptysis Patients by Thrombin and Fibrinogen-Thrombin Infusion Therapy Using a Fiberoptic Bronchoscope", Chest 1989 96(3):473-476.

Olschewski et al., "Inhaled iloprost for severe pulmonary hypertension", N. Engl J Med 2002 347(5):322-329.

Diringer et al., "Risk of thromboembolic events in controlled trials of rFVIIa in spontaneous intracerebral hemorrhage", Stroke 2008 39:850-856.

Gomberg-Maitland et al., "Prostacyclin therapies for the treatment of pulmonary arterial hypertension", Eur Respir J 2008 31:891-901.

Levy et al., "Recombinant factor VIIa in patients with coagulopathy secondary to anticoagulant therapy, cirrhosis, or severe traumatic injury:review of safety profile", Transfusion 2006 46:919-933.

(Continued)

*Primary Examiner*—Chih-mln Kam
(74) *Attorney, Agent, or Firm*—Licata & Tyrrell P.C.

(57) ABSTRACT

The present invention provides methods for the local treatment of tracheal, bronchial or alveolar bleeding or hemoptysis and/or reducing unwanted effects associated with systemic administration of thrombotic agents to a subject via intratracheal, intrabronchial or intraalveolar administration of a blood coagulation factor to the subject. Methods of the present invention are useful in treating diffuse alveolar hemorrhage secondary to blast lung injury, HIV infection and AIDS.

17 Claims, No Drawings

OTHER PUBLICATIONS

Mantzios et al. et al., "Massive pulmonary embolism after treatment with rFVIIa in a thrombocytopenic patient with acute myelogenous leukemia and intractable bleeding", European Journal of Haematology 2007 78:173-174.

Mazer et al., "Vascular injury and thrombotic potential:a note of caution about recombinant factor VIIa", Seminars in Cardiothoracic and Vascular Anesthesia 2007 11(4):261-264.

O'Connell et al., "Thromboembolic adverse events after use of recombinant human coagulation factor VIIa", JAMA 2006 295(3):293-298.

Powell et al., "Inhaled corticosteroid doses in asthma:an evidence-based approach", MJA 2003 178:223-225.

Cheer et al., "Inhaled tobramycin (TOBI) A review of its use in the management of *Pseudomonas aeruginosa* infections in patients with cystic fibrosis", Drugs 2003 63(22):2501-2520.

Palmer et al., "Aerosolized antibiotics and ventilator-associated tracheobronchitis in the intensive care unit", Crit Care Med 2008 36(7):2008-2013.

Waldeck, Bertil, "β-adrenoceptor agonists and asthma-100 years of development", European Journal of Pharmacology 2002 445:1-12.

Berntorp, E. "Recombinant FVIIa in the Treatment of Warfarin Bleeding" Seminars in Thrombosis and Hemostasis 2000 vol. 26(4): 433-435.

Diness et al. "Effect of Recombinant Human FVIIa on Warfarin-Induced Bleeding in Rats" Thrombosis Research 1990 vol. 59: 921-929.

Diness et al. "Recombinant Human Factor VIIa (rFVIIa) in a Rabbit Stasis Model" Thrombosis Research 1992 vol. 67: 233-241.

Holmberg et al. "Faster Onset of Effect and Greater Efficacy of NN1731 Compared with rFVIIa, aPCC and FvIII in Tail Bleeding in Hemophilic Mice" Journal of Thrombosis and Haemostasis 2009 vol. 7: 1517-1522.

Lauritzen et al. "Recombinant Human Factor VIIa and a Factor VIIa-Analogue Reduces Heparin and Low Molecular Weight Heparin (LMWH)-Induced Bleeding in Rats" Journal of Thrombosis and Haemostasis 2008 vol. 6: 804-811.

Chen et al. "Efficacy of Zymogen Factor VII Is Comparable to Activated Factor VII for Nonviral Gene Therapy Treatment of Hemophilia A" Blood 2005 vol. 106: Abstract 5543.

Emeis et al. "A Guide to Murine Coagulation Factor Structure, Function, Assays, and Genetic Alterations" Journal of Thrombosis and Haemostasis vol. 5: 670-679, (2007).

Petersen et al. "Characterization of Recombinant Murine Factor VIIa and Recombinant Murine Tissue Factor: A Human-Murine Species Compatibility Study" Thrombosis Research 2005 vol. 116: 75-85.

Petersen et al. "Plasma Elimination Kinetics for Factor VII Are Independent of Its Activation to Factor VIIa and Complex Formation with Plasma Inhibitors" Thrombosis and Haemostasis 2009 vol. 101: 818-826.

* cited by examiner

METHODS FOR PREVENTING AND TREATING LOCAL TRACHEAL, BRONCHIAL OR ALVEOLAR BLEEDING OR HEMOPTYSIS

PRIOR RELATED APPLICATIONS

This patent application is a continuation in-part of PCT/DK2005/000576, filed Sep. 9, 2005, which claims the benefit of priority from U.S. Provisional Application Ser. No. 60/693,969, filed Jun. 24, 2005, U.S. Provisional Application Ser. No. 60/622,977, filed Oct. 28, 2004 and U.S. Provisional Application Ser. No. 60/608,759, filed Sep. 10, 2004, each of which is incorporated herein by reference in its entirety.

FIELD OF THE INVENTION

The present invention provides methods to arrest clinically significant tracheal, bronchial or alveolar bleeding or hemoptysis, including, but not limited to persistent or recurrent bleeding conditions, acute bleeding conditions and chronic bleeding conditions. In the methods of the present invention, activated blood coagulation factors, i.e. hemostatic agents, other than thrombin or fibrinogen are administered intrabronchially, intratracheally or to the alveolar space via airway administration. These methods are useful in clinical medicine, especially critical or intensive care medicine and respiratory medicine. The methods of the present invention are also relevant to the fields of hematology, rheumatology, transplantation medicine, infectious diseases and oncology. In addition, the methods of the present invention can be used as prophylactics and/or preemptive therapies as well as in treatment of blast lung injury and lung bleeding and diffuse alveolar hemorrhage.

BACKGROUND OF THE INVENTION

Previous treatments for bronchial bleeding or hemoptysis comprise surgical and medical approaches. Among surgical approaches, local lesions can sometimes be treated by excision or cauterization via bronchoscopy, but this applies only to restricted numbers and classes of lesions. Among medical approaches, the most common is the systemic administration of blood platelets and/or blood coagulation factors, of which the patient may have a congenital or acquired deficiency, and/or the systemic administration of inhibitors of fibrinolytic (clot-dissolving) mechanisms. The latter include tranexamic acid, which inhibits the conversion of plasminogen to the fibrinolytic enzyme plasmin, and aprotinin, which inactivates fibrinolytic enzymes. The disadvantage of these medical approaches is that their effect is often inadequate to arrest the local bronchial and/or alveolar bleeding, especially if this is caused by a combination of one or more local lesions and a generalized deficiency of one or more hemostatic mechanisms or due to an affection of the alveolo-capillary membrane either of primary, unknown etiology or secondary to an identifiable systemic disease or condition, such as bone marrow transplantation, lung transplantation, chemotherapy, systemic autoimmune disease or infection. The inhibition of fibrinolysis can only arrest bleeding if the hemostatic mechanisms are adequate to form a blood clot in the first place. Bronchial and/or diffuse alveolar bleeding or hemoptysis is typically a medical emergency, in which rapid arrest of bleeding is required, often allowing insufficient time to identify the underlying causes with certainty, and in which treatment of the underlying disease is too retarded in comparison with the acute life-threatening hemorrhage. Medical treatments are therefore often given speculatively and without certainty of their efficacy.

Various methods of airway administration of substances intended to exert a therapeutic effect either locally or systemically or both have been the subject of both publications and patent applications. For example U.S. Pat. No. 3,920,845 discloses methods for treating allergic conditions with daily doses of 2-nitroindan-1,3-dione administered orally, parenterally or by insufflation. Methods for treating inflammation, allergic reactions and/or asthma via inhalation therapies are also disclosed in U.S. Pat. No. 5,980,865, U.S. Pat. No. 6,193,957, U.S. Pat. No. 6,497,877, and U.S. 2003/0195141 and U.S. Pat. No. 5,690,910 discloses intrabronchial administration of therapeutic agents for treatment of antigen-induced asthma. U.S. Pat. No. 5,427,797 discloses a method for administering nitric oxide by the inhalation route to prevent or treat blood platelet aggregation. U.S. Pat. No. 5,096,916 discloses administration of an imidazoline compound, which is a vasodilator and an alpha-adrenergic blocking agent, by inhalation for the treatment of symptoms of chronic obstructive pulmonary disease. US 2004/0265238 discloses an inhalable formulation of a hypertension reducing agent for treatment of pulmonary hypertension.

These patents serve to indicate the feasibility of drug delivery by airway administration, and thus their teachings are incorporated herein by reference in their entirety. However, the purpose of airway delivery of the administered substance(s) in the majority of these teachings has not been to arrest bleeding into the airway.

Gong et al. (U.S. 2005/0008580) disclose a method of treating hemophilia by the inhalation of aerosolized factor XI (FIX) of certain chemical characteristics and particle size, and the potential administration of factor VIII (factor VIII) in the same way is also disclosed, though not the subject of any claim. The purpose of this administration of FIX or factor VIII is to replace regular systemic administration of these factors in the long-term treatment of hemophilia, not to arrest bleeding into the airway.

Thrombin alone or thrombin together with fibrinogen has been applied intrabronchially by means of a bronchoscope to treat localized bleeding in the bronchial tree (Kinoshita et al., 1982; Tsukamoto et al., 1989; de Gracia et al., 1995; Saito et al., 1998; Hosoda et al., 2001; de Gracia et al., 2003). However, these results do not have predictive value for other coagulation factors that act at en earlier stage of the coagulation cascade. In the cited publications, thrombin and fibrinogen have been used as a specific surgical fibrin-forming "glue" to treat only those localized bleeding lesions that are accessible to the bronchoscope, and not bleeding from a wider area of the bronchoalveolar tree. On the other hand, general instillation or inhalation of thrombin and fibrinogen has not proved successful, incurring a risk of airway obstruction. It is therefore of therapeutic interest to use other coagulation factors acting at an earlier stage of the coagulation cascade and thus subject to local regulating influences to avoid an undesirably heavy deposition of fibrin glue in large parts of the airway. The present invention concerns the administration via the airway as an inhalant or via bronchoalveolar lavage other activated coagulant factors to treat both diffuse and localized bleeding in the airways. Methods of the present invention are particularly useful as prophylactics and/or preemptive treatments as well as a treatment of diffuse alveolar hemorrhage including but not limited to diffuse alveolar hemorrhage secondary to blast lung injury, HIV infection and AIDS.

SUMMARY OF THE INVENTION

In one aspect, the present invention relates to a method for arresting acute or recurrent or chronic tracheal, bronchial or alveolar bleeding or hemoptysis in a subject which comprises intratracheal, intrabronchial or intraalveolar administration to the subject of a blood coagulation factor which is not thrombin or fibrinogen.

In another aspect, the present invention relates to a method for preventing or inhibiting acute or recurrent or chronic tracheal, bronchial or alveolar bleeding or hemoptysis in a subject at risk for such bleeding which comprises intratracheal, intrabronchial or intraalveolar administration to the subject of a blood coagulation factor which is not thrombin or fibrinogen.

Accordingly, the invention relates to the use of a blood coagulation factor which is not thrombin or fibrinogen for the manufacture of a medicament for the treatment or prevention of acute or recurrent or chronic tracheal, bronchial or alveolar bleeding or hemoptysis in a subject, wherein said medicament is administered into the airway by various means including intratracheal, intrabronchial or intraalveolar administration.

Methods of the present invention are particularly useful as prophylactics and/or preemptive treatments for subject at risk for blast lung injury and/or diffuse alveolar hemorrhage and as treatments for subjects suffering from blast lung injury and/or diffuse alveolar hemorrhage.

An advantage of the present invention is that unwanted side effects or insufficient therapeutic effects of the systemic administration of thrombotic and/or hemostatic agents are reduced or avoided.

DETAILED DESCRIPTION OF THE INVENTION

The present invention relates to the intratracheal, intrabronchial or intraalveolar administration to a subject, preferably a mammal, more preferably a human and inclusive of both adults and children, blood coagulation factors other than thrombin or fibrinogen, preferably activated human factor VII and/or factor XIII to arrest bleeding from the trachea, bronchi or alveoli, or hemoptysis.

When used herein the term "blood coagulation factor other than thrombin or fibrinogen" includes all such factors other than thrombin or fibrinogen, including, but not limited to, factor VII, factor VIII, factor IX, factor V, factor XI, factor XIII, and any combination thereof.

When used herein, the term "factor VII" is intended to encompass factor VII polypeptides in their uncleaved (zymogen) form, as well as those that have been proteolytically processed to yield their respective bioactive forms, which may be designated factor VIIa. Typically, factor VII is cleaved between residues 152 and 153 to yield factor VIIa. When used herein in connection with factor VIIa, the term "variant" includes, without limitation, factor VII polypeptides that have either been chemically modified relative to human factor VIIa and/or contain one or more amino acid sequence alterations relative to human factor VIIa. Such variants may exhibit different properties relative to human factor VIIa, including stability, phospholipid binding, altered specific activity, and the like. A factor VIIa variant includes polypeptides that exhibit at least about 10%, preferably at least about 30%, more preferably at least about 50%, and most preferably at least about 70%, of the specific biological activity of human factor VIIa. For purposes of the invention, factor VIIa biological activity may be quantified by measuring the ability of a preparation to promote blood clotting using factor VII-deficient plasma and thromboplastin, as described, e.g., in U.S. Pat. No. 5,997,864. In this assay, biological activity is expressed as the reduction in clotting time relative to a control sample and is converted to "factor VII units" by comparison with a pooled human serum standard containing 1 unit of factor VII activity per ml. Alternatively, factor VIIa biological activity may be quantified by (i) measuring the ability of factor VIIa or a factor VIIa equivalent to produce activated factor X in a system comprising tissue factor embedded in a lipid membrane and factor X. Non-limiting examples of factor VIIa variants and the measurement of their biological activity have been set forth in WO2005074975, which is hereby incorporated by reference in its entirety. Further non-limiting examples of factor VIIa variants are polypeptides having at least 75% sequence identity to activated human factor VII, such as at least 85% sequence identity, e.g. at least 90% sequence identity, such as at least 95% sequence identity, e.g. at least 96% sequence identity, such as at least 98% sequence identity, e.g. at least 99% sequence identity to human factor VIIa.

By the terms "factor XIII" and "activated factor XIII" are meant the blood coagulation factor XIII and its activated forms as described in WO9315234, which is hereby incorporated by reference in its entirety. For convenience, the activated forms of factor XIII, factor XIII a'a and factor XIII a'a', are individually or collectively referred to as factor XIIIa. When used herein in connection with factor XIIIa, the term "variant" includes biologically active forms of factor XIIIa having at least about 10%, preferably at least about 30%, more preferably at least about 50%, and most preferably at least about 70%, of the specific biological activity of human factor XIIIa in an assay such as described by Dvilansky et al. (1970). Non-limiting examples of variants are polypeptides having at least 75% sequence identity to activated human factor XIII, such as at least 85% sequence identity, e.g. at least 90% sequence identity, such as at least 95% sequence identity, e.g. at least 96% sequence identity, such as at least 98% sequence identity, e.g. at least 99% sequence identity to activated human factor XIII.

Bleeding from the airways, including the trachea, bronchi or alveoli, or conditions covered by the more general term hemoptysis, may result from an acute condition, a recurrent condition or a chronic condition and may be due to lesions in the airways, whether caused by trauma, inflammation, infection or neoplasia, due to a congenital or an acquired disorder of the blood coagulation system or due to a combination of the aforementioned possible causes. For example, is it believed that the methods of the present invention will e.g. be useful in treating or preventing or inhibiting diffuse alveolar hemorrhage, including that due to blast lung injury and HIV infection or AIDS and treating or preventing or inhibiting chronic alveolar bleeding causing pulmonary hemosiderosis and subsequent chronic pulmonary insufficiency.

Blast lung injuries are categorized into four types: primary, secondary, tertiary and quaternary. Primary blast lung injuries are caused by barotraumas, either over pressurization or under pressurization relative to atmospheric pressure. Primary blast lung injuries most commonly involve, damage to the respiratory system. Secondary blast lung injuries are penetrating injuries from fragments, i.e. either as a result of the blast or as part of the weapon. Penetrating injuries are the leading cause of death in both civilian and military terrorist attacks. Tertiary blast lung injuries are those caused by structural collapse following an explosion, leading to blunt or crushing trauma. Finally, quaternary blast lung injuries refer to illnesses, injuries, and diseases related to the initial blast. These can range from toxic inhalation, burns, exposure to radiation, asphyxiation and inhalation of dust containing asbestos or coal.

Blast lung injuries cause disruption of the alveolar capillary interface. The subsequent alveolar inflammatory process induced by the mechanical stress to the lung tissue and the local pulmonary release of iron ions cause a severe inflammatory response with tissue factor expression in the distal airways. The pathophysiological process has been elucidated in autopsies performed on victims succumbed from blast lung injury. Blast lung injuries, particularly a blast lung injury in its severe forms has the concomitant combined features of bleeding and inflammation. Accordingly, blast lung injuries are considered a diffuse alveolar hemorrhage. Local treatment in the distal airways in accordance with the present invention preferably via the inhalation route or as a bronchoalveolar lavage causes fibrin formation via the binding of the drug to tissue factor expressed on alveolar macrophages and on the alveolar epithelium. Subsequently the drug-tissue factor complex activates coagulation factor VIIa which leads to activation of the coagulation cascade, i.e. thrombin activation and hence alveolar fibrin formation and thus hemostasis. The process from the initial blast trauma phase to tissue factor expression occurs within a few hours.

Accordingly, methods of the present invention are particularly useful as prophylactics, as pre-emptive treatments and as treatments for blast lung injuries.

For example, when used as a prophylactic, a blood coagulation factor other than thrombin or fibrinogen is administered intratracheally, intrabronchially or intraalveolar into the lung (airways) of persons, i.e. military personnel or civilians, exposed to a significant risk of forthcoming blast lung injuries. Local concentration of the blood coagulation factor after inhalation will be very high and maintained due to a long alveolar half life during risk of the blast lung injury.

For pre-emptive treatment, a blood coagulation factor other than thrombin or fibrinogen is administered intratracheally, intrabronchially or intraalveolar into the lung (airways) of persons, i.e. military personnel or civilians with a recent exposure (i.e. within a few hours) to a major blast injury but without manifest lung bleeding in the immediate post-explosion phase. Pre-emptive treatment is performed during the early induction phase from the primary injury to the induction of an inflammatory response and hence expression of tissue factor. This interval takes a few hours.

Treatment of manifest diffuse alveolar bleeding secondary to blast lung injury is performed in accordance with the present invention via intratracheal, intrabronchial or intraalveolar administration in nonintubated persons or a similar acceptable administration such as bronchoalveolar lavage in intubated victims with a solution of a blood coagulation factor other than thrombin or fibrinogen one or several times in order to control the diffuse alveolar bleeding after the blast injury.

In one embodiment, the subject treated is not a hemophilia patient.

When used herein the terms "intratracheal, intrabronchial or intraalveolar administration" include all forms of such administration whereby the coagulation factor is applied into the trachea, the bronchi or the alveoli, respectively, whether by the instillation of a solution of the factor, by applying the factor in a powder form, or by allowing the factor to reach the relevant part of the airway by inhalation of the factor as an aerosolized or nebulized solution or powder, with or without added stabilizers or other excipients.

In another embodiment, intratracheal, intrabronchial or intraalveolar administration does not include inhalation of the product but the instillation or application of a solution of the factor or a powder containing the factor into the trachea or lower airways.

Methods of intrabronchial/alveolar administration include, but are not limited to, bronchoalveolar lavage (BAL) according to methods well known to those skilled in the art, using as a lavage fluid a physiologically acceptable composition in which the blood coagulation factor or factors have been dissolved or indeed by any other effective form of intrabronchial administration including the use of nebulized powders containing the coagulation factor(s) or hemostatic agents in dry form, with or without excipients, or the direct application of the coagulation factor(s), excluding thrombin and fibrinogen, in solution or powder form during bronchoscopy. Methods for intratracheal administration include, but are not limited to, blind tracheal washing with a similar solution of dissolved blood coagulation factor(s), or the inhalation of nebulized fluid droplets containing the dissolved coagulation factor(s) obtained by use of any nebulizing apparatus adequate for this purpose.

The blood coagulation factors that are intended to be administered in this way comprise any of the coagulation factors other than thrombin and fibrinogen, preferably a coagulation factor necessary for local pulmonary hemostasis, and most preferably activated factor VII (factor VIIa), or a biologically active variant thereof, or a blood coagulation factor that promotes clot strength and resistance to fibrinolysis, such as factor XIII or factor XIIIa or a biologically active variant thereof. The blood coagulation factors are preferably purified and/or concentrated, and may e.g. be prepared from plasma or by means of recombinant DNA technology including expression in cell culture or transgenic animals.

The treatment with a blood coagulation factor that is not factor XIII or factor XIIIa may be combined with application of factor XIII or factor XIIIa, and optionally also with antifibrinolytic agents. Fibrinolytic activity is mediated by the binding of plasminogen to fibrin together with tissue-type plasminogen activator (t-PA), which promotes activation of the plasminogen to the active enzyme plasmin, resulting in digestion of fibrin in the clot and subsequently causing rebleeding. Factor XIIIa, a tetrameric transglutaminase formed from factor XIII by the action of thrombin, is an important mediator of clot resistance to fibrinolysis. Factor XIIIa augments clot stability by cross-linking fibrin, and thereby impedes fibrinolysis mediated by local plasmin activity. Administration of factor XIIIa or factor XIII, which is then activated in the body by thrombin, stabilizes the clot that has already been formed against mechanical, proteolytic and fibrinolytic activity.

Administration of coagulation factors by the intrabronchial route for the treatment of bronchial bleeding and hemoptysis in accordance with the present invention is demonstrated herein to be capable of arresting bronchial bleeding which was resistant to prior attempts of treatment by intravenous administration of the same coagulation factors. Alternative ways of administration are intratracheal administration and intraalveolar administration for arresting intratracheal bleeding or alveolar bleeding resulting from acute, recurrent or chronic conditions.

Thus, the present invention provides a significant improvement to the methods of treating tracheal, bronchial or alveolar bleeding. The methods of the present invention are particularly useful in preventing, inhibiting and/or treating diffuse alveolar hemorrhages including but not limited to the diffuse alveolar hemorrhaging which occurs secondary to blast lung injury, HIV infection or AIDS. Furthermore, intratracheal, intrabronchial or intraalveolar administration of coagulation factors is expected to avoid the potential unwanted thrombotic effects of systemic administration of coagulation factors such as recombinant human activated factor VII (rhFVIIa), whose intravenous use is potentially associated with a significant incidence of thrombosis.

A preferred embodiment of the present invention comprises local intrabronchial administration to human patients with persistent bronchial bleeding or hemoptysis of rhFVIIa by means of bronchoalveolar lavage with lavage fluid (e.g. 50 ml of isotonic saline) in which a suitable dose (e.g. at least 4.8 mg) of rhFVIIa has been dissolved, if necessary supplemented with a suitable dose (e.g. 625 U) of human blood coagulation factor XIII dissolved in the same fluid. This administration is optionally repeated at intervals depending on the recurrence of bronchial bleeding and is in some embodiments as short as one day or as long as 11 days or more if the treatment is successful. As supplementary or combinatorial treatments, the same coagulation factors can be given intravenously, preferably in the same or similar doses, as can the antifibrinolytic agents aprotinin and plasminogen activator inhibitor 1 (PAI-1), and the antifibrinolytic agents tranexamic acid or epsilon-aminocaproic acid can also be administered intrabronchially via a nebulizer.

Pharmaceutical compositions or formulations for use in the present invention include a factor VIIa preparation in combination with, preferably dissolved in, a pharmaceutically acceptable carrier, preferably an aqueous carrier or diluent. A variety of aqueous carriers may be used, such as 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

An aspect of the present invention and its preferred embodiment is the optional administration of human factor XIII or factor XIIIa, e.g. prepared from plasma or by means of recombinant DNA technology including expression in cell culture or transgenic animals, as supplementary therapy to stabilize the clot already formed as a consequence of factor VIIa that has been locally applied to the lungs. With respect to this adjuvant therapy, the factor XIII or factor XIIIa may be applied locally by the intratracheal, intrabronchial or intraalveolar methods specified above or may be administered systemically.

The following nonlimiting example is provided to further illustrate the present invention.

EXAMPLE

A 44-year-old man with chronic lymphatic leukemia received allogenic nonmyeloablative stem cell transplantation complicated by severe graft-versus-host disease requiring immunosuppressive medication at high dosage. The patient developed a systemic cytomegalovirus infection, treated with cidofir, which caused renal failure requiring hemodialysis. He then developed thrombocytopenia requiring daily blood platelet transfusions and subsequently developed clinical signs of bacterial sepsis and cardio-respiratory failure, which led to his admission to the intensive care unit. At this stage the platelet count was $45 \times 10^9$/ml, the activated partial thromboplastin time was prolonged at 57 seconds, and the prothrombin index and serum fibrinogen were normal. He was treated with antibiotics, inotropic agents and mechanical ventilation, which stabilized his condition over the following week. He then developed bronchial bleeding as evidenced by fresh blood in the intratracheal tube and an increased oxygen requirement. Platelet substitution raised a low platelet count of $10 \times 10^9$/ml to $128 \times 10^9$/ml without arresting the bleeding, which increased despite the administration of intravenous aprotinin and inhaled tranexamic acid. Over the following five weeks the intravenous administration rhFVIIa at doses of 2.4-9.6 mg alone or in conjunction with maximal doses of aprotinin, tranexamic acid and desmopressin were unsuccessful in arresting the persistent bronchial bleeding, although the platelet count was maintained above $50 \times 10^9$/ml and the coagulation status was normal apart from intermittent slight prolongation of the activated partial thromboplastin time. At this stage the treatment was changed according to the present invention, and rhFVIIa was given by bronchoalveolar lavage directly into the bronchial tree at a dose of 4.8 mg, supplemented with intravenous administration of the same dose of rhFVIIa. This arrested the bronchial bleeding for the first time, the effect lasting for 36 hours. Over the next 40 days the same treatment was repeated on nine occasions alone or in conjunction with intravenous aprotinin, in each case arresting the bleeding for a period of 24-48 hours. The blood coagulation status was unchanged and thromboelastography showed normal clot development and clot strength without evidence of hyperfibrinolysis in peripheral blood. At this stage intrabronchial administration of factor XIII 625 U by bronchoalveolar lavage was added to the treatment with intrabronchial and intravenous rhFVIIa, also supplemented with intravenous administration of the same dose of factor XIII. This arrested the bronchial bleeding for 11 days and reduced the increased oxygen requirement. A recurrence of bleeding was arrested for a further 7 days by repeating this treatment, and thereafter the patient was maintained free of bleeding by weekly intravenous administration of factor XIII.

REFERENCES CITED

U.S. Patent Documents

US 2005/0008580, Gong et al., Hemophilia treatment by inhalation of coagulation factors, filed Apr. 8, 2004.

Other Publications

Kinoshita M, Shiraki R, Wagai F, Watanabe H, Kitamura S (1982) Thrombin instillation therapy through the fiberoptic bronchoscope in cases of hemoptysis (in Japanese). Nihon Kyobu Shikkan Gakkai Zasshi 20:251-254.

Tsukamoto T, Sasaki H, Nakamura H (1989) Treatment of hemoptysis patients by thrombin and fibrinogen-thrombin infusion therapy using a fiberoptic bronchoscope. Chest 96:473-476.

de Gracia J, Mayordomo C, Catalan E, Vendrell M, Marti S, Bravo C (1995) The use of fibrinogen-thrombin via endoscope in the treatment of massive hemoptysis (in Spanish). Arch Bronconeumol 31:227-232.

Saito Y, Mikami M, Nakamura S, Hashimoto N, Abe Y, Baba M, Takizawa J, Kawakami M, Kamei K (1998) Pulmonary pseudallescheriasis in a patient with diabetes mellitus and alcoholic liver cirrhosis (in Japanese). Nihon Kokyuki Gakkai Zasshi 36:498-502.

Hosoda H, Ooi K, Tsukahara T, Inaki E, Kataoka Y, Chin S, Sunamori M (2001) Frequent fiberscopic bronchial lavage for a case of bilateral severe pulmonary contusion with flail chest (in Japanese). Kyobu Geka 54:352-354.

de Gracia J, de la Rosa D, Catalan E, Alvarez A, Bravo C, Morell F (2003) Use of endoscopic fibrinogen-thrombin in the treatment of severe hemoptysis. Respir Med 97:790-795.

Dvilansky A, Britten A F, Loewy A G (1970) Factor XIII assay by an isotope method. I. Factor XIII (transamidase) in plasma, serum, leucocytes, erythrocytes and platelets and evaluation of screening tests of clot solubility. Br J Haematol 18:399-410.

The invention claimed is:

1. A method of treating diffuse alveolar hemorrhage in a subject in need of such treatment comprising administering an effective amount of activated blood coagulation factor VII (FVIIa) or a variant thereof to the subject by intratracheal, intrabronchial or intraalveolar administration so that bleeding is arrested, said variant exhibiting at least 50% of the ability of FVIIa to promote blood clotting using factor VII-deficient plasma and thromboplastin or to produce activated factor X in a system comprising tissue factor embedded in a lipid membrane and factor X and having at least 90% sequence identity to human FVIIa.

2. The method of claim 1 wherein the diffuse alveolar hemorrhage is secondary to blast lung injury, HIV infection or AIDS.

3. The method of claim 2 wherein the FVIIa or a variant thereof is administered to a subject at risk for blast lung injury.

4. The method of claim 2 wherein the FVIIa or a variant thereof is administered to a subject suffering from blast lung injury, HIV infection or AIDS prior to diffuse alveolar hemorrhage.

5. The method of claim 2 wherein the FVIIa or a variant thereof is administered to a subject suffering from diffuse alveolar hemorrhage secondary to blast lung injury, HIV infection or AIDS to treat the diffuse alveolar hemorrhaging.

6. The method of claim 1, wherein the subject is administered a solution of FVIIa or a variant thereof via bronchoalveolar lavage.

7. The method of claim 1, wherein the subject is administered a solution of FVIIa or a variant thereof via blind tracheal washing.

8. The method of claim 1, wherein the subject is administered a nebulized solution of FVIIa or a variant thereof via inhalation.

9. The method of claim 1, wherein the subject is administered a nebulized powder form of FVIIa or a variant thereof via inhalation.

10. The method of claim 1, wherein the subject is administered FVIIa or a variant thereof by direct application of FVIIa or a variant thereof during bronchoscopy.

11. The method of claim 1, wherein the subject is a mammal.

12. The method of claim 11, wherein the mammal is a human treated with FVIIa or a variant thereof.

13. The method of claim 12, wherein the human is a child younger than 12 years of age.

14. The method of claim 12, wherein the human is an adult older than 12 years of age.

15. The method of claim 1, wherein the subject is administered FVIIa or a variant thereof in combination with factor XIII or activated factor XIII as a supplementary therapy.

16. The method of claim 15, wherein the factor XIII or activated factor XIII is administered systemically.

17. The method of claim 15, wherein the factor XIII or activated factor XIII is administered via intratracheal, intrabronchial or intraalveolar administration.

* * * * *